United States Patent [19]

Makovec et al.

[11] Patent Number: 5,500,430
[45] Date of Patent: Mar. 19, 1996

[54] AMIDIC DERIVATIVES OF GLUTAMIC, ASPARTIC AND 2-AMINO ADIPIC ACIDS, A PROCESS FOR PREPARING SAME, AND ANTI-GASTRIN COMPOSITION CONTAINING THE DERIVATIVES

[75] Inventors: Francesco Makovec; Luigi A. Rovati; Lucio C. Rovati, all of Monza, Italy

[73] Assignee: Rotta Research Laboratorium S.p.A., Milan, Italy

[21] Appl. No.: 74,818

[22] PCT Filed: Dec. 6, 1991

[86] PCT No.: PCT/EP91/02342

§ 371 Date: Jun. 10, 1993

§ 102(e) Date: Jun. 10, 1993

[87] PCT Pub. No.: WO92/10479

PCT Pub. Date: Jun. 25, 1992

[30] Foreign Application Priority Data

Dec. 11, 1990 [IT] Italy .................. 67995 A/90

[51] Int. Cl.$^6$ .................. A61K 31/46; C07D 221/20
[52] U.S. Cl. .................. 514/278; 546/16
[58] Field of Search .................. 514/278; 546/16

[56] References Cited

U.S. PATENT DOCUMENTS 4,791,215 12/1988 Rovati et al. .................. 562/433
5,064,853 11/1991 Gasc et al. .................. 514/419

FOREIGN PATENT DOCUMENTS 0383690 8/1990 European Pat. Off. .
2160869 1/1986 United Kingdom .
9106529 5/1991 WIPO .

OTHER PUBLICATIONS

European Journal of Medicinal Chemistry. Chimica Therapeutica, vol. 21, No. 1, Jan. 1986, France "new glutamic and aspartic derivatives with potent CCK–antagonistic activity" by F. Makovec et al. pp. 9–20.

*Primary Examiner*—Yogendra N. Gupta
*Attorney, Agent, or Firm*—Sughrue, Mion, Zinn, Macpeak & Seas

[57] ABSTRACT

Amidic derivatives of glutamic, aspartic and 2-amino adipic acids represented by the following formula (I):

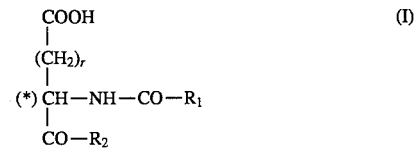

wherein r is from 1 to 3, $R_1$ is an aryl group or a substituted aryl group, $R_2$ is a 8-azaspiro(4.5)decan-8-yl group or a 3-azaspiro(5.5)decan-3-yl group, wherein said compound has a chiral center marked with an asterisk in said formula (I), thus forming a racemic (R,S) form or an isomeric form. The amidic derivatives are useful in treating ulcers, hypergastrinaemia-activated tumors, pathological conditions of CNS, biliary dyskinesia, colitis, pancreatistis, and surgically induced myosis.

10 Claims, No Drawings

AMIDIC DERIVATIVES OF GLUTAMIC, ASPARTIC AND 2-AMINO ADIPIC ACIDS, A PROCESS FOR PREPARING SAME, AND ANTI-GASTRIN COMPOSITION CONTAINING THE DERIVATIVES

The subject of the present invention is compounds with activities antagonistic towards gastrin or other peptides related thereto, which can be represented by the general formula indicated below:

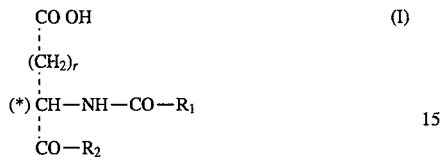

in which r is from 1 to 3, and $R_1$ is selected from mono-, di-substituted phenyl groups, in which the substituents are selected from chlorine, linear and branched C1–C4 alkyl groups, cyano, nitro, methoxy, and trifluoromethyl groups, the 2(beta)-naphthyl group, and heterocyclic, monocyclic and bicyclic groups containing 1 heteroatom such as nitrogen, oxygen or sulphur and selected from furyl, thiophenyl, pyrrolyl, pyridinyl, and pyridinyl-N-oxide groups unsubstituted or mono- or disubstituted with methyl and chlorine, indolyl (2- or 3-yl), thionaphthyl (2- or 3-yl), benzofuranyl (2- or 3-yl), quinolinyl (2- or 3-yl), or isoquinolinyl (3-yl) groups and in which $R_2$ is selected independently from:

1) a heterocyclic spiro group represented by

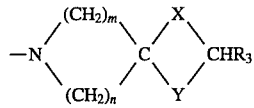

in which m and n are selected independently and may assume values between 1 and 3 provided that the ring formed consists of at least 5 atoms, x and y are selected independently from $(CH-R_3)_z$, $(CH=CH)$, $TCH_2$ and $CH_2T$ in which T is O, S, NH—C(O) or C(O)—NH, and in which $R_3$ is a group selected independently from H, $CH_3$, $C_2H_5$, $OCH_3$, $OC_2H_5$, $CH_2OH$ and OH and z may assume values of from 0 to 3, provided that the ring formed consists of at least 3 atoms.

2) a bicyclic spiro amino group represented by:

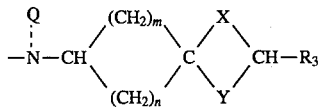

in which m, n, x, y and $R_3$ have the meanings given in point 1 above and Q maybe selected independently from H and $CH_3$.

3) a bicyclic amino group (condensed) represented by:

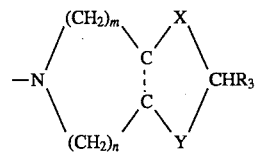

in which m and n are selected independently and may assume values of between 1 and 3 and x, y and $R_3$ have the meanings given in point 1 above.

4) a bicyclic amino group (condensed) represented by:

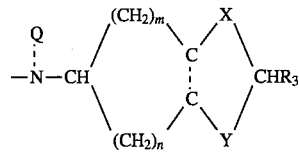

in which m and n are selected independently and may assume values of between 1 and 3 and x, y $R_3$ and Q have the meanings given in point 1 above.

5) an adamantyl alkylamino group represented by:

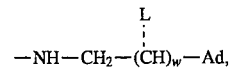

w is between 0 and 2, L is H, a methyl or methoxyl group and Ad is an adamantyl (1- or 2-yl) group.

The stereochemistry of the compounds claimed at the chiral centre marked with an asterisk in the formula (I) may be racemic (R, S) or, preferably, rectus (R); r is preferably 2, $R_1$ is preferably selected from the group consisting of 3-chloro-phenyl and 3,5-dichlorophenyl, and $R_2$ is preferably Selected from the group consisting of 8-azaspiro[4.5] decan-8-yl and 1-adamantyl-2-aminoethane.

The compounds of the present invention show potent antagonistic activity towards gastrin ("little gastrin" or G-17) and towards pentagastrin, which is its biologically active terminal peptide sequence.

Gastrin is a polypeptide hormone secreted by the cells of the antral and duodenal mucosae, its secretion being induced, in particular, by a nervous mechanism by means of vagal excitation.

Once secreted, the gastrin reaches the parietal cells, which are situated mainly in the fundic mucosa, via the bloodstream and activates the receptors of the cell membranes by binding thereto. This activation starts the process of the formation of HCl and its secretion into the gastric cavity.

Hyperactivity of this system results in the hypersecretion of plastric acid, which may have consequences which are harmful to the organism but can be eliminated with the use of specific antagonists.

The compounds of the invention show a high level of activity against the secretion of acid in vivo in the various animal species tested, blocking the secretory stimulus induced by pentagastrin in a dose-dependent manner. The activity is specific, since it does not block secretions induced by carbachol or histamine.

As already stated, the compounds can therefore be used, to advantage, in the treatment and prevention of various diseases in man, for example, ulcers or gastro-duodenitis resulting from excessive gastric secretion induced by a hypergastrinaemic condition, in Zollinger-Ellison syndrome, or in the treatment of some kinds of tumours which are activated by hypergastrinaemia, in which it is advantageous to block gastrin's activity in stimulating the secretion of acid.

On the basis of the considerable activity they show in vitro as inhibitors of the binding of gastrin at the level of the CNS, the compounds of the invention might also be shown to be effective for some kinds of mental disorders attributable to an imbalance in the physiological neuron levels of gastrin or other bioactive peptides related thereto such as, for example, cholecystokinin (CCK).

The remarkable anti-CCK activity of some of the compounds of the invention, which depends in particular on suitable substitutions at $R_1$, combined with their antigastrin activity, could also make them particularly suitable for treating diseases in man such as biliary diskinesia, Coliris, pancreatitis or for the treatment and prevention of some eye conditions such as, for example, myosis induced in the course of the surgical treatment of cataracts or by chronic eye inflammation.

The method of preparing the compounds of the invention which have their chiral centres in the R (rectus) form is characterised by steps which may be represented as follows:

a) reacting the gamma-benzyl ester of N-carbobenzoxy-D-glutamic acid with an amine of the formula H—$R_2$, in which $R_2$ has the meaning given above, by the mixed anhydride method, in an inert anhydrous solvent at a temperature between −15° and +15° to give the compounds of formula (III), (see the diagram below)

b) debenzylating and decarbobenzoxylating the compound of formula (III), dissolved in an inert solvent, in a single step by reacting it with hydrogen at ambient temperature and atmospheric pressure in the presence of a catalytically effective quantity of a hydrogenation catalyst to produce the derivatives of formula (II) (see the diagram below), c) reacting the derivatives of formula (II) under Schotten-Bauman conditions with a equivalent quantity of an acyl chloride of the formula $R_1$—COCl, in which $R_1$ has the meaning given above, at a temperature from 0° to 15° C. and recovering the amides of formula (I) from the reaction mass.

The series of steps of the method according to the invention is illustrated as a whole by the following diagram:

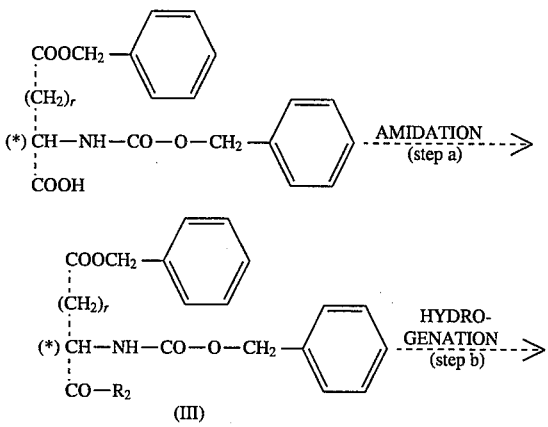

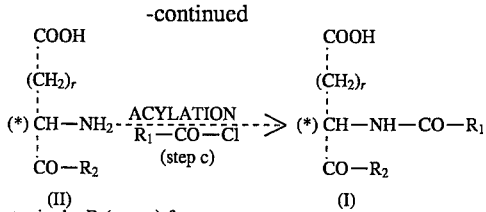

(*) chiral centre in the R (rectus) form

The amidation step (a) is carried out at a temperature preferably between −15° and −10° C. for from 1 to 24 hours, preferably 6 hours, with a stoichiometric ratio between the reagents. The preferred solvent for effecting the reaction is selected from chloroform, dioxane and tetrahydrofuran.

The hydrogenation step (b) is preferably carried out in the presence of between 0.02 and 0.001 atoms of palladium per mole of compound (III), supported on carbon, in methanolic solution at ambient temperature and pressure in a stream of hydrogen for a period of from 1 to 12 hours, preferably 6 hours. The acylation step (c) is preferably carried out at a temperature of about 5° C. for from 1 to 24 hours, preferably 12 hours.

The following examples are given to illustrate the invention further.

EXAMPLE 1

Preparation of the gamma-benzyl ester of (R) 4-carbobenzoxy-amino-5-(8-azaspiro[4.5]decan-8-yl)-5-oxopentanoic acid, (compound $A_1$ in Table A).

37.1 g (0.1 moles) of the gamma-benzyl ester of N-carbobenzoxy-D-glutamic acid were dissolved in 250 ml of anhydrous tetrahydrofuran, the solution was cooled to −10° C. and 10.1 g (0.1 moles) of triethylamine were added with stirring; 10.8 g (0.1 moles) of ethyl chloroformate were then added, still at −10° C. The temperature was kept at −10° C. for 20 minutes and 13.9 g (0.1 moles) of 8-azaspiro[4.5]decane were then added. The mixture was stirred for a further 6 hours whilst the temperature rose to ambient temperature; the mixture was then evaporated to dryness and the residue taken up with ethyl acetate.

It was then washed with 2N HCl, sodium bicarbonate and, finally, with water and then dried over anhydrous $Na_2SO_4$. Concentration to a small volume produced an oily residue. The crude product thus obtained was pure enough to be used directly in the subsequent step without further purification.

TLC: Rf 0.59 (benzene-ethyl acetate 7/3: v/v) Product 39.4 g. Yield 80%.

All the compounds of formula III were synthesised by the same method (see the diagram above). Table A below shows some of the compounds obtained with some of their identifying characteristics.

TABLE A derivatives of the formula

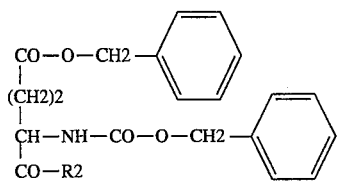

| COMPOUNDS | R2 | FORMULA | MELTING POINT (°C.) | TLC (Rf) Benzene Ethyl acetate 7:3 (V/V)] |
|---|---|---|---|---|
| A1 | 8-Azaspiro[4.5]decan-8-yl | C29H36N2O5 | oil | 0.59 |
| A2 | 3-Azaspiro[5.5]undecan-3-yl | C30H38N2O5 | oil | 0.54 |
| A3 | 2-Azaspiro[4.4]nonan-2-yl | C28H34N2O5 | oil | 0.39 |
| A4 | 2-Azaspiro[4.5]decan-2-yl | C29H36N2O5 | oil | 0.41 |
| A5 | 3-Amino-spiro[5.5]undecano | C31H40N2O5 | oil | 0.66 |
| A6 | 1.4-dioxa-8-Azaspiro[4.5]decan-8-yl | C27H32N2O7 | oil | 0.26 |
| A7 | Isoquinolin-2-yl-decahydro | C29H36N2O5 | oil | 0.48 |
| A8 | 1-Adamantyl-2-amino-ethane | C32H40N2O5 | 76–77 | 0.66 |

EXAMPLE 2

Preparation of (R) 4-amino-5-(8-azaspiro [4.5]decan-8 -yl)-5-oxopentanoic acid, (compound $B_1$ in Table B).

All the compounds of formula II were synthesised by the same method (see diagram).

Table B below shows the compounds thus obtained with some of their identifying characteristics.

TABLE B derivatives of the formula

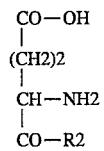

| COMPOUNDS | R2 | FORMULA | MELTING POINT (°C.) | TLC (Rf) [ButOH-Acetic Acid H2O: 5/2/2 (V/V)] | Rotary power [α]D (3% in MetOH) |
|---|---|---|---|---|---|
| B1 | 8-Azaspiro[4.5]decan-8-yl | C14H24N2O3 | 174–175 | 0.54 | −10° |
| B2 | 3-Azaspiro[5.5]undecan-3-yl | C15H26N2O3 | 142–143 | 0.64 | −11.2° |
| B3 | 2-Azaspiro[4.4]nonan-2-yl | C13H22N2O3 | 130–131 | 0.63 | −8.3° |
| B4 | 2-Azaspiro[4.5]decan-2-yl | C14H24N2O3 | 136–137 | 0.58 | −9.6° |
| B5 | 3-Amino-spiro[5.5]undecano | C16H28N2O3 | 142–143 | 0.57 | −11.7° |
| B6 | 1.4-dioxa-8-Azaspiro[4.5]decan-8-yl | C12H20N2O5 | 149–150 | 0.45 | −14° |
| B7 | Isoquinolin-2-yl-decahydro | C14H24N2O3 | 160–161 | 0.71 | −8.6° |
| B8 | 1-Adamantyl-2-amino-ethane | C17H28N2O3 | 169–170 | 0.82 | −7.3° |

49.2 g (0.1 moles) of the benzyl ester of (R) 4-carbobenzoxy-amino-5-(8-azaspiro[4.5]decan-8-yl-5-oxopentanoic acid (compound A1) were dissolved in 500 ml of methanol, to which 1 g of 10% palladiated carbon had been added, and hydrogenated with a stream of hydrogen at ambient temperature for 6 hours. The catalyst was filtered out and the methanol distilled under vacuum. The oily residue obtained (row 286.4) crystallised when taken up with acetone, and was filtered out to give a compound with a chromatographic purity greater than 95%.

TLC: Rf 0.54 [n-butanol-acetic acid-$H_2O$ 5/2/2 (V/V)]. Melting-point: 174°–175° C. Rotatory power: (alpha)$^{20}$D= −10° (c=3% in methanol). Product 23.6 g. Yield 88%.

EXAMPLE 3

Preparation of 4-[3-(chlorobenzoyl)-amino]-5-(8-azaspiro 4.5]decan-8-yl)-5-oxopentanoic acid (R=rectus). (Compound C-1 in Table C).

26.8 g (0.1 moles) of (R) 4-amino-5-(8-azaspiro[4.5] decan-8-yl)-5-oxopentanoic acid (compound B1 ) were suspended in 300 ml of water and then dissolved with stirring by the addition of 10.6 g (0.1 moles) of sodium carbonate. 17.5 g (0.1 moles) of 3-chlorobenzoyl chloride were then added over a period of 1 hour at 0° C. with stirring.

The mixture was left to react for 12 hours.

The mixture was then acidified to Congo red with dilute HCl and the precipitate thus formed was filtered out and crystallised with acetonitrile.

M.P.: 145°–146° C. TLC [methylene chloride-ethanol 1:1 (V/V)]: Rf 0.81 Product 33.4 g Formula: $C_{21}H_{27}ClN_2O_4$ (mw 406.9) Yield 82%. Rotatory power: $[alpha]^{20}_D = -15°$ C. (c=3.0% in methanol).

All the compounds of formula I (see diagram) were synthesised by the same method.

Table C below shows the compounds thus obtained with some of their identifying characteristics, as well as the yields obtained (calculated for the method as a whole).

HPLC analysis was used to check the optical purity of the compounds obtained by the stereo-conservative synthesis method described above with the use of an ODS-C-18 column as the stationary phase, 0.025M phosphate buffer (pH 6.5)-acetonitrile as the mobile phase, and L-phenylalaninamide as the differentiating solvent.

The compounds given in Table C were found, in all cases, to have optical purities greater than 95%. The compound C1, for example, had a retention time of 11.45 minutes and an optical purity of 99.6% under the conditions described. For comparison, the compound C-32, which is an S-series (sinister) derivative and is the optical antipode of the compound C1, has a retention time of 10.8 minutes under the same experimental conditions.

TABLE C derivatives (D series) of the formula

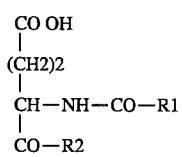

| COMPOUNDS | R1 | R2 | FORMULA | MELTING POINT (°C.) |
|---|---|---|---|---|
| C1 | 3-chloro-phenyl | 8-Azaspiro[4.5]decan-8-yl | C21H27ClN2O4 | 149–150 |
| C2 | 3-chloro-phenyl | 3-Azaspiro[5.5]undecan-3-yl | C22H29ClN2O4 | 94–95 |
| C3 | 3-chloro-phenyl | 2-Azaspiro[4.4]nonan-2-yl | C20H25ClN2O4 | 69–70 |
| C4 | 3-chloro-phenyl | 2-Azaspiro[4.5]decan-2-yl | C21H27ClN2O4 | 88–89 |
| C5 | 3,5-dichloro-phenyl | 8-Azaspiro[4.5]decan-8-yl | C21H26Cl2N2O4 | 185–186 |
| C6 | 3,5-dichloro-phenyl | 2-Azaspiro[4.5]decan-2-yl | C21H26Cl2N2O4 | 112–113 |
| C7 | 3,5-dichloro-phenyl | 2-Azaspiro[4.4]nonan-2-yl | C20H24Cl2N2O4 | 111–113 |
| C8 | 3,5-dichloro-phenyl | 8-Azaspiro[4.5]decan-8-yl | C21H26Cl2N2O4 | 91–92 |
| C9 | 2,3-dichloro-phenyl | 8-Azaspiro[4.5]decan-8-yl | C21H26Cl2N2O4 | 105–167 |
| C10 | 2-Naphthyl | 8-Azaspiro[4.5]decan-8-yl | C25H30N2O4 | 145–147 |
| C11 | 3-methyl phenyl | 8-Azaspiro[4.5]decan-8-yl | C22H30N2O4 | 148–150 |
| C12 | 3-ethyl phenyl | 8-Azaspiro[4.5]decan-8-yl | C23H32N2O4 | 119–120 |
| C13 | 3,5-dimethyl phenyl | 8-Azaspiro[4.5]decan-8-yl | C23H32N2O4 | 183–185 |
| C14 | 3-nitrophenyl | 8-Azaspiro[4.5]decan-8-yl | C21H27N3O6 | 182–183 |
| C15 | 3-methoxy phenyl | 8-Azaspiro[4.5]decan-8-yl | C22H30N2O5 | 115–116 |
| C16 | 3-cyano phenyl | 8-Azaspiro[4.5]decan-8-yl | C22H27N3O4 | 154–155 |
| C17 | 3-trifluoromethyl phenyl | 8-Azaspiro[4.5]decan-8-yl | C22H27F3N2O4 | 122–123 |
| C18 | 4-isopropyl phenyl | 8-Azaspiro[4.5]decan-8-yl | C24H34N2O4 | 157–158 |
| C19 | quinolinyl (3-yl) | 8-Azaspiro[4.5]decan-8-yl | C24H29N3O4 | 104–105 |
| C20 | 3,4-dichloro-phenyl | 3-Azaspiro[5.5]undecan-3-yl | C22H28Cl2N2O4 | 91–92 |
| C21 | quinolinyl (3-yl) | 3-Azaspiro[5.5]undecan-3-yl | C25H31N3O4 | 119–120 |
| C22 | 3-chlorophenyl | 3-amino-spiro[5.5]undecano | C23H31ClN2O4 | 145–146 |
| C23 | 3,5-dichloro-phenyl | 3-amino-spiro[5.5]undecano | C23H30Cl2N2O4 | 103–105 |
| C24 | furyl(2-yl) | 8-Azaspiro[4.5]decan-8-yl | C19H26N2O5 | 98–99 |
| C25 | 2-chloro pyridyl (3-yl) | 8-Azaspiro[4.5]decan-8-yl | C20H26ClN3O4 | 167–168 |
| C26 | indolyl (2-yl) | 8-Azaspiro[4.5]decan-8-yl | C23H29N3O4 | 194–195 |
| C27 | 3-chlorophenyl | 1,4-dioxa-8-azaspiro[4.5]decan-8-yl | C19H23ClN2O6 | 72–73 |
| C28 | 3,5-dichloro-phenyl | 1,4-dioxa-8-azaspiro[4.5]decan-8-yl | C19H22Cl2N2O6 | 110–111 |
| C29 | 3-chlorophenyl | isoquinolin-2- | C21H27ClN2O4 | 84–85 |

TABLE C-continued

| | | | | |
|---|---|---|---|---|
| C30 | 3-chlorophenyl | decahydro 1-adamantyl-2-amino ethane | C24H31ClN2O4 | 185–186 |
| C31 | 3,5-dichlorophenyl | 1-adamantyl-2-amino ethane | C24H30Cl2N2O4 | 179–182 |
| C32 (**) | 3-chlorophenyl | 8-Azaspiro[4.5]decan-8-yl | C21H27ClN2O4 | 138–139 | derivatives (D series) of the formula

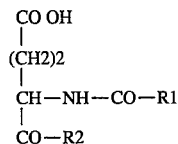

| COMPOUNDS | CRYSTALLISATION SOLVENT | TLC (Rf) methylene-chloride-Ethanol 1:1 (V/V) | Rotatory power [α]D (3% in MetOH) | Yield % (*) |
|---|---|---|---|---|
| C1 | Acetonitrile | 0.81 | −15.0° | 60 |
| C2 | Acetonitrile | 0.78 | −18.4° | 55 |
| C3 | Acetonitrile-H2O(4:1) | 0.66 | −14.7° | 45 |
| C4 | Acetonitrile-Isopr. ether (5:1) | 0.73 | −16.6° | 54 |
| C5 | Acetonitrile | 0.80 | −11.9° | 61 |
| C6 | Acetonitrile-Acetone (1:1) | 0.81 | −15.0° | 56 |
| C7 | Acetonitrile | 0.79 | −12.0° | 48 |
| C8 | Acetonitrile | 0.76 | −18.4° | 68 |
| C9 | Acetonitrile | 0.87 | −8.5° | 63 |
| C10 | Acetonitrile | 0.86 | −29.5° (**) | 44 |
| C11 | Acetonitrile | 0.90 | −13.3° | 53 |
| C12 | Acetonitrile | 0.77 | −14.8° | 48 |
| C13 | EtOH-H2O (1:1) | 0.93 | −11.8° | 47 |
| C14 | Acetonitrile | 0.75 | −13.3° | 53 |
| C15 | Acetonitrile | 0.91 | −18.3° | 36 |
| C16 | Acetonitrile | 0.73 | −18.5° | 45 |
| C17 | Acetonitrile | 0.76 | −15.0° | 35 |
| C18 | Acetonitrile | 0.89 | −18.3° | 48 |
| C19 | Acetonitrile-H2O (5:1) | 0.42 | −10.0° | 43 |
| C20 | Acetonitrile | 0.85 | −19.2° | 52 |
| C21 | Acetonitrile | 0.45 | −9.6° | 58 |
| C22 | Acetonitrile | 0.84 | −10.0° | 59 |
| C23 | Acetonitrile | 0.88 | −12.2° | 57 |
| C24 | Acetonitrile-isopr. ether (1:4) | 0.75 | −9.3° | 53 |
| C25 | Acetonitrile | 0.69 | −5.3° | 49 |
| C26 | Acetonitrile | 0.80 | −8.2° | 23 |
| C27 | Acetonitrile-isopr. ether (1:1) | 0.68 | −13.4° | 44 |
| C28 | Acetonitrile | 0.67 | −15.6° | 50 |
| C29 | Acetonitrile | 0.64 | −19.5° | 56 |
| C30 | Acetonitrile | 0.75 | +9.6° (NaOH) | 58 |
| C31 | Acetonitrile-H2O (5:1) | 0.76 | +11.7° (NaOH) | 55 |
| C32 (**) | Acetonitrile | 0.80 | +14.5° | 52 |

TABLE C-continued (*) The yield shown is the overall yield calculated for the method as a whole, starting from the benzyl ester of N-carbobenzoxy-D-glutamic acid
(**) Rotatory power in CHCl₃
(**) The compound C32 is an S-series (sinister) derivative which is the optical antipode of the compound C1 and is shown for comparison.

The method of preparing the derivatives of the invention which have chiral centres in the racemic form (R, S) is characterised by steps which may be represented as follows:

a) reacting an internal anhydride of the formula:

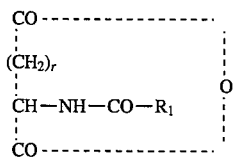

in which r and $R_1$ have the meanings given above, prepared by conventional methods as already described in the literature [Makovec et al., Eur.J.Med.Chem. 21 (1986), 9–20] with an amine of the formula H—$R_2$, in 26.8 g (0.1 moles) of (D, L) 3-chlorobenzoyl glutamic anhydride were loaded into a reactor and suspended in 100ml of water.

The suspension was cooled to about 5° C. and 35 g (0.2 moles) of 1,4-dithia-8-azaspiro[4.5]decan-8-yl were added dropwise over a period of about 15 minutes. The mixture was left to react for 3 hours at this temperature and acidified with glacial acetic acid. It was then filtered, washed with water until neutral, and dried. The crude product thus obtained was crystallised with acetonitrile. 32.3 g were obtained.

Formula: $C_{19}H_{23}ClN_2O_4S_2$ (mw 442.8) Yield 73%. M.P.: 169°–17° C. TLC (isoamyl alcohol-acetone-$H_2O$: 5/2/1 -V/V): Rf 0.79.

Some of the compounds thus synthesised are given by way of example in Table D below with some of their identifying characteristics as well as the yields obtained.

TABLE D (R, S Series) derivatives of the formula

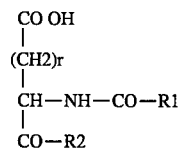

| COMPOUNDS | R1 | R2 | r | FORMULA | MELTING POINT (°C.) | CRYSTALLISATION SOLVENT | TLC isoamyl alcohol acetone-H2O: 5:2:1 (V/V) | YIELD % |
|---|---|---|---|---|---|---|---|---|
| D1 | 3 chlorophenyl | 1,4-dithia-8-Azaspiro[4.5]decan-8-yl | 2 | C19H23ClN2O4S2 | 169–170 | Acetonitrile | 0.79 | 73 |
| D2 | 3-chlorophenyl | 1,4-dioxa-2-hydroxymethyl 8-azaspiro[4.5]decan-8-yl | 2 | C20H25ClN2O7 | 138–140 | Acetonitrile | 0.51 | 48 |
| D3 | 3-chlorophenyl | 1-oxa-4-thia-8-azaspiro[4.5]decan-8-yl | 2 | C19H23ClN2O5S | 168–169 | Acetonitrile | 0.63 | 70 |
| D4 | 3-chlorophenyl | 8-Azaspiro[4.5]decan-8-yl | 1 | C20H25ClN2O4 | 108–109 | Acetonitrile | 0.60 | 66 |
| D5 | 3-chlorophenyl | 8-Azaspiro[4.5]decan-8-yl | 3 | C22H29ClN2O4 | 95–98 | Acetonitrile isopropyl ether (1:1) | 0.81 | 38 |
| D6 | 3-chlorophenyl | 2-amino-naphthalene-decahydro | 2 | C22H29ClN2O4 | 216–217 | Ethanol | 0.71 | 57 |
| D7 | 3,5-dichloro-phenyl | 2-amino-naphthalene-decahydro | 2 | C22H28Cl2N2O4 | 246–247 | Ethanol | 0.84 | 53 | which $R_2$ has the meaning given above, in a molar ratio of from 1 to 5 in a solvent such as water, ethyl acetate, dioxane, acetonitrile, tetrahydrofuran, or a mixture thereof, at a temperature between −20° and 30° C. and recovering the compounds of formula I from the reaction mass by fractional crystallisation or other conventional methods.

The following example is given below to illustrate the invention further.

Preparation of (R,S) (±)-4-[(3-chlorobenzoyl) amino]-5-(1.4-dithia-8-azaspiro[4.5]decan-8-yl)-5-oxopentanoic acid. (Compound $D_1$ of Table D)

An analysis of the pharmacological activities of the compounds of the invention with regard, in particular, to their activities against acid secretion performed by an antigastrin mechanism, was then carried out by means of a series of pharmacological tests carried out both in vivo and in vitro and is documented below.

Antisecretive activity in anaesthetised rats

Antisecretive activity in rats was determined with the use of male animals each weighing about 200 g, anaesthetised with urethane. Gastric secretion was stimulated with pentagastrin. The method of K. S. Lai (Gut 5, (1964), 327–341) was used, slightly modified.

After tracheotomy, cannulae were inserted in the oesophagus and the duodenum. A tepid solution. (37° C.) of 0.25 mM NaOH was perfused and passed through the stomach by means of a peristaltic pump at a constant flow rate of 1 ml/minute. After stabilisation for 20 minutes, the stimulating agent, dissolved in a physiological solution, was perfused for 120 minutes at a dose of 30 mcg/Kg/h in a volume of 0.95 ml/hour. After perfusion for 60 minutes (the basal stimulation), the product under test was administered as an intravenous bolus (I.V.) and the perfusion of the stimulant continued for a further 60 minutes. Acid secretion was recorded continuously as a function of time.

The activity of the product was evaluated as the percentage reduction in the secreted acidity after the administration of the product compared with the base acidity measured during the first 60 minutes of collection during which only the pentagastrin was present.

Different doses of the antagonist compounds tested were administered so that an ID50, that is, the dose (in mg/Kg I.V.) capable of inhibiting the effect of pentagastrin by 50%, could be calculated.

The results thus obtained are illustrated in the following table (Table 1) in which the activities of the compounds are expressed as the ID50s under the stimulus of 30 mcg/Kg/h of pentagastrin.

TABLE 1

Antagonistic activity (ID50 mg/Kg IV) towards gastric acid secretion induced by pentagastrin (30 mcg/Kg/h) in rats

| COMPOUND C1 | 20 | COMPOUND C21 | IN (>75) |
|---|---|---|---|
| COMPOUND C2 | 33 | COMPOUND C22 | 55 |
| COMPOUND C3 | 75 | COMPOUND C23 | 40 |
| COMPOUND C4 | 49 | COMPOUND C24 | IN (>75) |
| COMPOUND C5 | 15 | COMPOUND C25 | 69 |
| COMPOUND C6 | 45 | COMPOUND C26 | IN (>75) |
| COMPOUND C7 | 60 | COMPOUND C27 | 81 |
| COMPOUND C8 | 41 | COMPOUND C28 | 70 |
| COMPOUND C9 | 40 | COMPOUND C29 | 35 |
| COMPOUND C10 | 45 | COMPOUND C30 | 25 |
| COMPOUND C11 | 38 | COMPOUND C31 | 20 |
| COMPOUND C12 | 38 | COMPOUND C32 | IN (>100) |
| COMPOUND C13 | 33 | COMPOUND D1 | IN (>75) |
| COMPOUND C14 | 68 | COMPOUND D2 | 85 |
| COMPOUND C15 | 46 | COMPOUND D3 | 67 |
| COMPOUND C16 | 66 | COMPOUND D4 | 70 |
| COMPOUND C17 | 55 | COMPOUND D5 | 32 |
| COMPOUND C18 | 28 | COMPOUND D6 | 60 |
| COMPOUND C19 | 68 | COMPOUND D7 | 48 |
| COMPOUND C20 | 64 | Proglumide | 500 |
| | | Lorglumide | IN (>100) |

The antigastrin activity was particularly favourable in the case of the glutamic acid (r=2) derivatives and when $R_1$ was 3-chlorophenyl or 3,5-dichlorophenyl and when the amine group $R_2$ was the azaspiro[4.5]-8-yl group or the 2-amino-1-adamantyl ethyl group (see compounds C1, C5, C30 and C31). It should be noted that, in this experimental model, the most active of the compounds of the invention were about 30 times more active than the reference antigastrin compound proglumide. It is also interesting to note that the CCK antagonist lorglumide is completely inactive up to a dose of 100 mg/Kg, as is the compound C-32 which is the S-series optical antipode of the compound C-1, showing that the antigastrin activity is stereospecific. The activity of these compounds against gastric secretion is linked specifically to their antigastrin activity. In fact, they have neither anticholinergic nor antihistamine (anti $H_2$) activity since, in the experimental model described above, they were completely inactive when carbachol (30 mcg/Kg/h) or histamine (2.3 mg/Kg/h) were used as the stimulants. The activity seems even more remarkable if one takes account of the low toxicity of the compounds of the invention. For example, in rats, the compound C5 has an LD50 IV of about 400 mg/Kg. The average lethal dose (LD50) in this case is therefore about 25 times greater than the antigastrin dose (the ID50) for the same method of administration.

Antisecretive activity in conscious dogs

In order to confirm the antigastrin activity in rats, some of the most active compounds claimed were to be tested in a second animal species, the dog, in order to exclude species-specific phenomena.

Male beagles weighing about 10 Kg were used and carried gastric fistulae at the level of the greater curvature, connected near the antral region, steel cannulae 5 cm long and 2 cm wide being inserted for collecting the gastric juices externally. After a period of about one month to recover from the operation, and after suitable conditioning, the animals were treated with pentagastrin at a dose of 3 mcg/Kg/h. The Stimulant, dissolved in a physiological solution, was perfused into the femoral vein for 180 minutes at a rate of 1.9 ml/h. After perfusion for 60 minutes (the basal stimulation) the product under test, dissolved in a physiological solution (1 ml/Kg), was administered in a bolus into the contra-lateral vein and, at the same time, the perfusion of the stimulant continued for a further 120 minutes. The acid secretion was recorded continuously as a function of time.

The activity of the product was evaluated as the percentage reduction in the secreted acidity after the administration of the product compared with the base acidity measured during the first 60 minutes of collection during which only the pentagastrin was present, for each of the periods 0–60 and 60–120 minutes after the product had been administered in a bolus.

Different doses of the compounds (C-1 and C-5) tested were administered so that an ID50, that is the dose (in mg/Kg I.V.) capable of inhibiting the effect of the pentagastrin by 50% could be calculated.

The results obtained are given in the following table (Tab. 2) in which the % variations from the base (the mean ± standard deviations calculated on the values obtained from 4 animals) are given for the various doses administered under the stimulus of 3 mcg/Kg/h of pentagastrin, as well as the activities of the compounds, calculated as their ID50s, and the correlation coefficients of the regression lines calculated on the basis of the experimental data.

TABLE 2

Antagonistic activity (ID50 mg/Kg IV) towards gastric acid secretion induced by pentagastrin (30 mcg/Kg/h) in conscious dogs carrying gastric fistulae

| COM-POUND | DOSE (mg/Kg) | Variation % (Mean ± SD) from base (0–60 min) | |
|---|---|---|---|
| | | (period 60–120 min) | (period 120–180 min) |
| C1 | 5 | −18.2 ± 0.3 | −22.8 ± 16.7 |
| | 10 | −38.9 ± 7.9 | −14.3 ± 8.5 |
| | 20 | −49.5 ± 4.2 | −26.1 ± 6.4 |
| | 30 | −61.1 ± 12.5 | −56.7 ± 19.5 |
| | 40 | −63.4 ± 11.5 | −43.4 ± 10.3 |
| | 60 | −74.2 ± 5.6 | −79.9 ± 1.6 |
| | | ID50 mg/Kg = 19.7 | ID50 mg/Kg = 31.5 |
| | | (n = 6; r = 0.995) | (n = 6; r= 0.83) |
| C5 | 5 | −36.0 ± 16.3 | −20.5 ± 13.1 |
| | 10 | −59.5 ± 5.0 | −31.9 ± 1.3 |
| | 30 | −67.8 ± 4.8 | −48.1 ± 1.7 |
| | | ID50 mg/Kg = 8.9 | ID50 mg/Kg = 32.5 |
| | | (n = 3; r = 0.916) | (n = 3; r = 0.998) |

[r = regression correlation coefficient calculated an n values]

The compounds C-1 and C-5 were shown also to be potent inhibitors of gastric acid secretion induced by pentagastrin in dogs. In fact, they block the acid output during the first hour after their administration in a bolus in a dose-dependent manner with ID50s of about 20 and 10 mg/Kg for the compounds C-1 and C-5, respectively.

The activity remains noteworthy even during the second hour after the intravenous administration of the bolus (during the period 120–180 minutes) with an ID50 of about 30 mg/Kg for both compounds.

IN VITRO TESTS

Tests on binding to cerebral cortex membranes of mice

The capacities of some of the compounds of the invention to inhibit the binding of pentagastrin to the gastrin receptor sites on the cerebral cortex membranes of mice was to be evaluated. Pentagastrin tritiate[ beta-alanyl-3-3H(N)] was used as the ligand.

Mouse cortical tissue Was homogenised cold in 20 volumes of tris buffer (pH 7.7). After washing and centrifuging, the final pellet was resuspended in 20 volumes of binding buffer containing, inter alia, TRIS, BSA and Bacitracin. 0.4 ml of the membrane thus obtained were then incubated with a radioactive tracer and the compounds under test for 40 minutes at 37° C.

After the supernatant liquid had been removed by centrifuging, the radioactivity associated with the pellet was determined with a liquid scintillator (a beta-counter). The specific binding was the difference between the binding in the absence and in the presence of 10-5M pentagastrin.

The results obtained are given in Table 3 which gives the IC50s of the compounds tested, that is, the concentration (in moles/liter) of the antagonist which can displace 50% of the pentagastrin tritiate from the receptor.

It can be seen from the data given in Table 3 that some of the compounds of the invention are potent inhibitors of the binding of pentagastrin to the receptors of the cortical membranes of mice. The most active compounds are in fact about 10 times less potent than the specific antagonist (pentagastrin) and about 100 times more potent than the CCK-antagonist lorglumide. The derivatives belonging to the R series (for example, the compound C-1) were about 50 times more active than the corresponding S enantiomers (compare the compounds C1 and C32).

In general, there is some correlation between the peripheral and central antigastrin activities of the compounds of the invention, and this leads to the assumption that the two types of receptors are quite similar. However, the two types of activity, that is the inhibition of gastric secretion stimulated by pentagastrin (see Table 1) and the inhibition of the binding of pentagastrin to the cortical membranes (see Table 3) do not always completely correspond. Thus, for example, the compound C1 which is about 1.5 times more active than the compound C2 on the peripheral gastrin (gastric secretion) receptor is only one third as active as C2 centrally. Similarly, the compound C5, which is slightly more active than the compound C-30 as a peripheral pentagastrin inhibitor is three times less active than that compound on the central receptor.

The considerable activity of some of the compounds of the invention in displacing pentagastrin from the central receptor sites may be assumed to be of possible practical interest since it suggests the possible use of the products of the invention in the treatment of cerebral disorders attributable to an imbalance in the physiological neuron levels of gastrin.

TABLE 3

Inhibition of the binding of pentagastrin [β-alanyl-3-3H(N)] - to mouse cortical membranes

| COMPOUNDS | IC50 (moles/liter) | COMPOUNDS | IC50 (moles/liter) |
| --- | --- | --- | --- |
| Pentagastrin | $2.5 \times 10^{-9}$ | C23 | $3.2 \times 10^{-7}$ |
| C1 | $4.7 \times 10^{-7}$ | C29 | $8.0 \times 10^{-7}$ |
| C2 | $1.4 \times 10^{-7}$ | C30 | $3.0 \times 10^{-8}$ |
| C5 | $1.1 \times 10^{-7}$ | D1 | $2.6 \times 10^{-6}$ |
| C6 | $3.2 \times 10^{-7}$ | D2 | IN ($>10^{-5}$) |
| C8 | $2.0 \times 10^{-7}$ | D4 | $6.8 \times 10^{-6}$ |
| C10 | $1.0 \times 10^{-7}$ | D5 | $1.5 \times 10^{-6}$ |
| C14 | $8.1 \times 10^{-6}$ | Lorglumide (1) | $6.1 \times 10^{-6}$ |
| C21 | $5.1 \times 10^{-7}$ | C32 (1) | $2.6 \times 10^{-5}$ |

Note (1): these compounds were tested for comparison

Anticholecystokinin (anti-cc, K) activity

In order to confirm the hypothesis that the molecular conformations of the compounds of the invention are suitable to provide them with antagonistic activity towards CCK as well as towards gastrin, the anticontracturant activities of some of the compounds of the invention were tested on guinea-pig gall bladders stimulated by CCK-8 in vitro.

A longitudinal strip of guinea-pig gall bladder was placed in a bath for isolated organs in the presence of Krebs at a temperature of 32° C. and oxygenated continuously with an oxygen-$CO_2$ mixture (95-5 V/V).

The isometric contractions were detected by means of a force transducer and recorded.

The gall bladder was contracted with the use of a concentration of 10 ng/ml of CCK-8; the antagonistic activities of the compounds towards the contracturant effect of the CCK was determined with the use of different concentrations, thus determining the IC50 values, that is, the concentration of the compound in mcg/ml which can antagonise the contracturant effect of CCK by 50%.

The results obtained are given in the following table which shows the compounds tested and the IC50s found, which were calculated by the regression method on a set of at least 3 tests for each compound tested.

TABLE 4

Anti-CCK activity (concentration 10 ng/ml) expressed as the IC50 IN mcg/ml on guinea pig gall bladders in vitro.

| COMPOUND | ACTIVITY IC50 mcg/ml) |
| --- | --- |
| C1 | 20 |
| C2 | 4.9 |
| C3 | 43 |
| C5 | 34.8 |
| C8 | 1.7 |
| C10 | 1.0 |
| C19 | 1.5 |
| C20 | 0.5 |
| C21 | 0.2 |
| C29 | 234 |
| C30 | 59 |
| D2 | 108 |
| D4 | 36 |
| Lorglumide | 0.06 |

It can be seen from an examination of the table that some of the compounds claimed, such as, for example, the compounds C-8, C-10,C-19, C-20 and C-21, antagonise the contracturant activity of CCK-8 at concentrations no greater than those shown by lorglumide which was the specific CCK antagonist selected for comparison.

Inhibitory effect on the rate of growth of tumorous colic cells induced by pentagastrin Gastrin has a trophic effect on the digestive epithelium. The chronic administration of gastrin (or pentagastrin, the biologically active portion of the physiological hormone) to rats causes hyperplasia of the fundic and colic mucosae. It has recently been shown that gastrin stimulates the growth of a transplantable mouse colic tumour produced by chemical induction [Winsell et al. —Surgical Forum, 33, 384 (1982)].

Upon the basis of this premise, it was wished to investigate whether the gastrin-specific antagonists of the invention could antagonise the growth of experimentally-induced gastrointestinal tumours.

One of the gastrin antagonists of the invention which was amongst the most active in the tests described above, that is the compound C-5, was selected for this purpose. Male mice weighing 20–25 g were inoculated subcutaneously in the interscapular region with a suspension of $8 \times 10^4$ tumour cells of a mouse colic adenocarcinoma.

4 groups each of 8 animals were used, that is: a control group, a group of animals which were treated with pentagastrin 250 mcg/Kg twice a day, and two groups of animals which were treated with the compound C-5 at doses of 3 and 10 mg/Kg i.p. respectively twice a day in addition to pentagastrin as described above.

After 21 days, the animals were killed and the fundic mucosa and the tumours were removed, weighed and extracted to determine the DNA. The results obtained are given in Table 5 below.

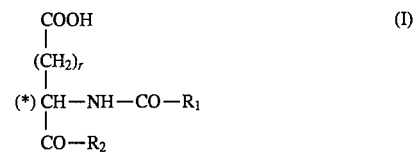

wherein r is from 1 to 3, $R_1$ is an substituted or unsubstituted aryl group, $R_2$ is a 8-azaspiro(4.5)decan 8-yl group or a 3-azaspiro(5.5)undecan-3-yl group, wherein said compound has a chiral center marked with an asterisk in said formula (I), thus forming a racemic (R,S) form or an isomeric form, or a pharmaceutically acceptable salt thereof.

2. The compound according to claim 1, wherein the compound is the (R) isomer.

3. A compound according to claim 1, wherein r is 2, $R_1$ is a 3-chlorophenyl group or 3,5dichlorophenyl group, $R_2$ is a 8-azaspio(4.5)decan-8-yl group or a 3-azaspiro(5.5)undecan-3-yl group, wherein said compound has chiral center marked with an asterisk in said formula (I), thus forming a racemic (R,S) form or an isomeric form.

4. A pharmaceutical preparation including, as an active ingredient, a pharmaceutically effective amount of at least one compound according to claim 1 or a pharmaceutically acceptable salt thereof, and a pharmaceutically active carrier.

5. The composition according to claim 4, wherein said pharmaceutically acceptable carrier is selected from the group consisting of a vehicle, a binder, a flavoring, a

TABLE 5

Antagonistic activity of the compound C-5 on colic tumorous growth induced by pentagastrin

| GROUPS | No. ANIM. | WEIGHT OF THE MUCOSA FUNDICA Mean (mg) ± SD | Student's t-test | FUNDIC DNA Mean (mg) ± SD | Student's t-test |
|---|---|---|---|---|---|
| A): Control | 8 | 18.4 ± 1.95 | — | 0.237 ± 0.03 | — |
| B): Pentagastrine (PEG) | 8 | 32.0 ± 3.50 | VsA: 10.3 (*) | 0.330 ± 0.05 | VsA: 4.96 (*) |
| C): PEG + C–5 (3 mg/Kg- 2 × dle) | 8 | 23.85 ± 3.48 | VsA: 3.34 () VsB: 4.35 (*) | 0.268 ± 0.03 | VsA: 2.39 (*) VsB: 3.47 (**) |
| D): PEG + C–5 (10 mg/Kg- 2 × dle) | 8 | 18.90 ± 2.54 | VsA: 0.52 VsB: 9.21 (*) | 0.252 ± 0.03 | VsA: 1.06 VsB: 4.17 (*) |

| GROUPS | No. ANIM. | WEIGHT OF THE COLIC TUMOR Mean (mg) ± SD | Student's t-test | TUMOROUS DNA Mean (mg) ± SD | Student's t-test |
|---|---|---|---|---|---|
| A): Control | 8 | 520.1 ± 36.2 | — | 2.73 ± 0.35 | — |
| B): Pentagastrine (PEG) | 8 | 657.0 ± 97.7 | VsA: 3.97 () | 3.62 ± 0.50 | VsA: 4.42 (*) |
| C): PEG + C–5 (3 mg/Kg- 2 × dle) | 8 | 601.5 ± 91.7 | VsA: 2.49 (*) VsB: 1.25 | 3.24 ± 0.42 | VsA: 2.05 (*) VsB: 1.74 |
| D): PEG + C–5 (10 mg/Kg- 2 × dle) | 8 | 554 ± 61.7 | VsA: 1.44 VsB: 2.69 (*) | 2.94 ± 0.31 | VsA: 1.36 VsB: 3.51 (**) |

(*): P < 0.05
(**): P <0.01
(***): P <0.001

The data of Table 5 show that pentagastrin induces significant hyperplasia in the fundic mucosa and a significant increase in the weight of the colic tumour and the DNA content. The compound C-5 can inhibit both the aforementioned trophic effects of pentagastrin in a significant and dose-dependent manner.

We claim:

1. A compound represented by the following formula (I):

dispersant, a preservative, a humectant, and mixtures thereof.

6. A method for treating ulcers comprising administering to a subject in need of such treatment, a pharmaceutically effective amount of at least one compound according to claim 1 or a pharmaceutically acceptable salt thereof.

7. A method for treating hypergastrinaemia-activated gastro-intestinal or pancreatic adenocarinomas comprising adminstering, to a subject in need of such treatment, a pharmaceutically effective amount of at least one compound according to claim 1 or a pharmaceutically acceptable salt thereof.

8. A method for treating pathological conditions of CNS attributable to an imbalance in the physiological neuron levels of gastrin or cholecystokinin comprising adminstering, to a subject in a need of such treatment, a pharmaceutically effective amount of at least one compound according to claim 1 or a pharmaceutically acceptable salt thereof.

9. A method for treating biliary dyskinesia, colitis and pancreatitis comprising administering, to a subject in need of such treatment, a pharmaceutically effective amount of at least one compound according to claim 1 or a pharmaceutically acceptable salt thereof.

10. A method for treating and preventing myosis induced by surgical treatment for cataracts or by chronic eye inflammation comprising administering, to a subject in need of such treatment, a pharmaceutically effective amount of at least one compound according to claim 1 or a pharmaceutically acceptable salt thereof.

\* \* \* \* \*